(12) United States Patent
Rothstein et al.

(10) Patent No.: US 7,758,580 B2
(45) Date of Patent: Jul. 20, 2010

(54) COMPOUND BIPOLAR ABLATION DEVICE AND METHOD

(75) Inventors: Paul T. Rothstein, Elk River, MN (US); Roderick E. Briscoe, Rogers, MN (US); David E. Francischelli, Brooklyn Park, MN (US); David J. S. Kim, Maple Grove, MN (US); Alison Lutterman, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1119 days.

(21) Appl. No.: 11/143,400

(22) Filed: Jun. 2, 2005

(65) Prior Publication Data

US 2006/0036236 A1 Feb. 16, 2006

Related U.S. Application Data

(60) Provisional application No. 60/576,245, filed on Jun. 2, 2004.

(51) Int. Cl.
*A61B 18/12* (2006.01)

(52) U.S. Cl. .............................. 606/51; 606/41; 606/48; 606/50; 606/52

(58) Field of Classification Search .................. 606/1, 606/27, 48–52, 205–208
See application file for complete search history.

(56) References Cited

U.S. PATENT DOCUMENTS

| | | | |
|---|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |

(Continued)

FOREIGN PATENT DOCUMENTS

WO 99/23960 5/1999

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Linda C Dvorak
*Assistant Examiner*—Jaymi Della
(74) *Attorney, Agent, or Firm*—Mike Jaro; Jeffrey J. Hohenshell

(57) ABSTRACT

Method and apparatus for ablating target tissue adjacent pulmonary veins of a patient. The ablation device can include a lower jaw assembly including a proximal jaw having a proximal electrode and a distal jaw having a distal electrode, and an upper jaw assembly including an upper jaw having an upper electrode. A proximal actuator can be movable between a first position in which the proximal jaw is open and a second position in which the proximal jaw is clamped with respect to the upper jaw. A distal actuator can be movable between a third position in which the distal jaw is open and a fourth position in which the distal jaw is clamped with respect to the upper jaw.

15 Claims, 9 Drawing Sheets

U.S. PATENT DOCUMENTS

| | | |
|---|---|---|
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,147,373 A * | 9/1992 | Ferzli .................... 606/144 |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowle |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |

| Patent No. | Date | Inventor |
|---|---|---|
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,063,081 A | 5/2000 | Mulier et al. |
| 6,071,279 A | 6/2000 | Whayne et al. |
| 6,088,894 A | 7/2000 | Oakley et al. |
| 6,096,037 A | 8/2000 | Mulier et al. |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier et al. |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,270,497 B1 | 8/2001 | Sekino et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,794 B1 * | 11/2002 | Trapp et al. .................. 606/45 |
| 6,484,727 B1 | 11/2002 | Vaska et al. |
| 6,488,680 B1 | 12/2002 | Francischelli |
| 6,500,176 B1 | 12/2002 | Truckai et al. |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier et al. |
| 6,537,272 B2 | 3/2003 | Christopherson et al. |
| 6,558,382 B2 | 5/2003 | Jahns et al. |
| 5,697,536 C1 | 6/2003 | Eggers et al. |
| 6,584,360 B2 | 6/2003 | Francischelli |

| | | |
|---|---|---|
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey et al. |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey et al. |
| 6,858,028 B2 | 2/2005 | Mulier |
| 6,887,238 B2 | 5/2005 | Jahns |
| 6,899,711 B2 | 5/2005 | Stewart |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2003/0040745 A1* | 2/2003 | Frazier et al. ............... 606/51 |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044335 A1* | 3/2004 | de la Torre et al. ............ 606/27 |
| 2004/0044340 A1 | 3/2004 | Francischelli |
| 2004/0049179 A1 | 3/2004 | Francischelli |
| 2004/0073210 A1* | 4/2004 | Taniguchi et al. ............ 606/51 |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0113821 A1* | 5/2005 | Pendekanti et al. .......... 606/41 |
| 2005/0131392 A1* | 6/2005 | Chu et al. .................... 606/1 |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Chrisitian |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29 (abstract only).

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease,"The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Diesase,"The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3945.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg. 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

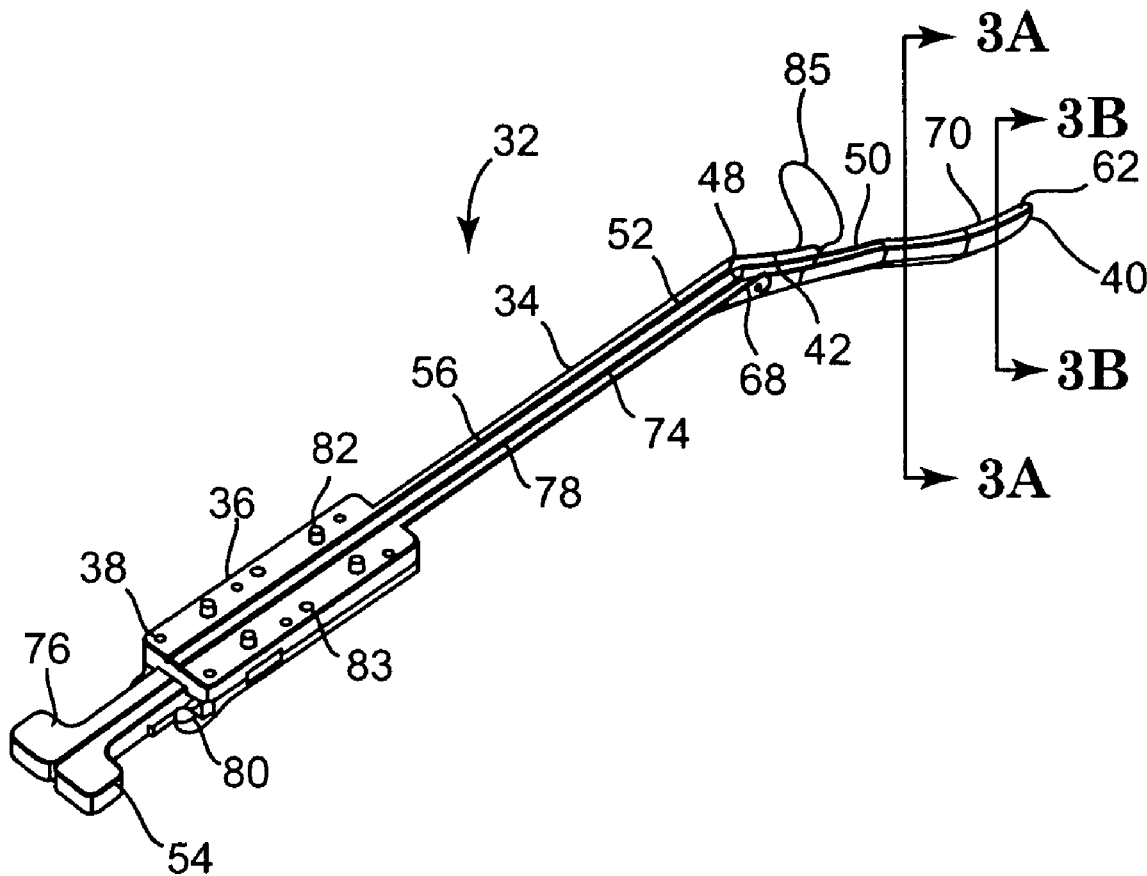
Fig. 3
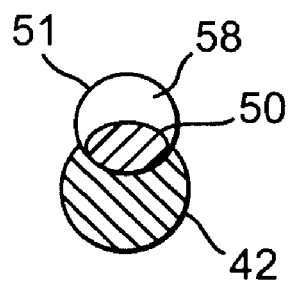 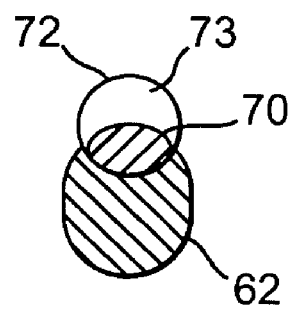
Fig. 3A          Fig. 3B

COMPOUND BIPOLAR ABLATION DEVICE AND METHOD

RELATED APPLICATIONS

This application claims the benefit of the filing date of U.S. Provisional Patent Application No. 60/576,245 filed on Jun. 2, 2004, which is incorporated herein by reference in its entirety.

BACKGROUND

Various types of electrocautery devices are used for ablating tissue. Typically, such devices include a conductive tip or blade which serves as one electrode in an electrical circuit which is completed via a grounding electrode coupled to the patient. With sufficiently high levels of electrical energy between the two electrodes, heat is generated which is sufficient to denature proteins within the tissue and cause cell death.

By controlling the energy level, the amount of heat generated and the degree of tissue damage can also be controlled. High levels of voltage can actually cut and remove tissue (i.e., electrosurgery), while lower levels will simply create sufficient heat to cause cell damage, but leave the structure intact (i.e., catheter ablation) and block electrical pathways within the tissue. Irrigation of the electrode(s) with saline or other conductive fluid can decrease the interface impedance, cool the tissue and allow for a greater lesion depth.

The treatment of chronic atrial fibrillation (AF) requires the creation of numerous linear lesions that extend completely through the thickness of the tissue. Some electrophysiologists have created these lesions using a tip electrode of standard ablation catheters. These catheters were designed to create spot lesions, typically for ablation of specific structures or focal abnormalities. In order to make the linear lesions required to replicate the MAZE procedure, an electrophysiologist makes a series of focal lesions, and "connects the dots."

Manufacturers have therefore developed catheters that have a linear array of electrodes along a long axis (i.e., the Amazr, MECCA, and Revelation catheters). The catheter and electrodes can be positioned in contact with the tissue and either individually or sequentially apply energy to each electrode. Additionally, catheters which incorporate an electrode which is energized and moves along the length have been proposed.

Surgeons have also been able to create linear lesions on the heart using applications of the same techniques. For example, Kottkamp et al. in an article entitled "Intraoperative Radiofrequency Ablation of Chronic Atrial Fibrillation: A Left Atrial Curative Approach by Elimination of Anatomic 'Anchor' Reentrant Circuits," *Journal of Cardiovascular Electrophysiology*, 1999; §10:772-780 disclosed using a hand-held device that creates as series of spot or short (<1 cm) linear lesions. Other investigators have used long, linear unipolar probes to create somewhat longer lesions, such as described by Shirmoikd E. et al. in an article entitled "In Vivo and In Vitro Study of Radio-Frequency Application with a New Long Linear Probe: Implication for the MAZE Procedure," *Journal of Thoracic and Cardiovascular Surgery*, 2000; §120:164-72. Still others have used multi-electrode linear catheters, similar to those described above to create a series of ablations that net a linear lesion, as described by Melo J. et al. in an article entitled "Endocardial and Epicardial Radiofrequency Ablation in the Treatment of Atrial Fibrillation with a New Intra-Operative Device," *European Journal of Cardio-Thoracic Surgery*, 2000; §18:182-186.

U.S. patent application Ser. No. 10/015,690, in the names of Francisichelli et al. describes a bipolar ablation device that integrates an electrode into jaws of a hemostat-like or forceps-like device, known as the Cardioblate-BP. This results in a tool that can clamp and ablate the tissue in between the jaws. In conjunction with a transmurality algorithm, this configuration is amenable to creating transmural lesions. However, the Cardioblate-BP was designed to access the heart via a mid-line sternotomy. In order for the therapy to be considered as stand-alone, access must be made less invasively. Simply placing the Cardioblate-BP jaw onto an endoscopic handle has certain advantages, but there are significant limitations when trying to manipulate both jaws simultaneously through separate tissue spaces.

A microwave device that can loop around the posterior of the heart to encircle the pulmonary veins has been developed. A right thorocotomy is created at about the fourth intercostal space, and the pericardium is freed behind the superior vena cava and the inferior vena cava. A moveable antenna slides within an integral sheath and discrete sections are ablated in series is described by Saltman, "AE in a Completely Endoscopic Approach to Microwave Ablation for Atrial Fibrillation," *Heart Surgery Forum*, 2003, 6(3):E38-E41.

Today, the MAZE procedure is performed with traditional cut and sew techniques. The market is demanding quicker, safer and less invasive approaches. Many companies are developing ablation techniques that heat (or cool) and thermally destroy the underlying tissue. Methods of chemical ablation have also been proposed.

SUMMARY OF THE INVENTION

Accordingly, there is a need for a method and device that results in less trauma to the patient, fewer insertions and removals of the ablation tools, and more flexibility for selecting ablation configurations using a single tool to ablate target tissue of a patient's heart. A need also exists for a compound bipolar ablation device for minimally-invasive isolation of the pulmonary veins without completely occlude blood flow.

Some embodiments of the invention provide an ablation device for ablating target tissue adjacent pulmonary veins of a patient. The ablation device can include a lower jaw assembly including a proximal jaw having a proximal electrode and a distal jaw having a distal electrode, and an upper jaw assembly including an upper jaw having an upper electrode. A proximal actuator can be movable between a first position in which the proximal jaw is open and a second position in which the proximal jaw is clamped with respect to the upper jaw. A distal actuator can be movable between a third position in which the distal jaw is open and a fourth position in which the distal jaw is clamped with respect to the upper jaw.

Embodiments of a method of the invention can include inserting a lower jaw assembly through an incision in the patient and inserting an upper jaw assembly through the incision. The method can include coupling the upper jaw assembly to the lower jaw assembly. The method can also include moving at least one of a proximal actuator and a distal actuator in order to position at least one of a proximal jaw and a distal jaw with respect to an upper jaw and providing ablation energy to at least one of an upper electrode, a proximal electrode, and a distal electrode.

BRIEF DESCRIPTION OF THE DRAWINGS

FIGS. 3, 3A, and 3B are perspective and cross-sectional views of a lower jaw assembly of a compound bipolar ablation device according to one embodiment of the invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

Figure 1:
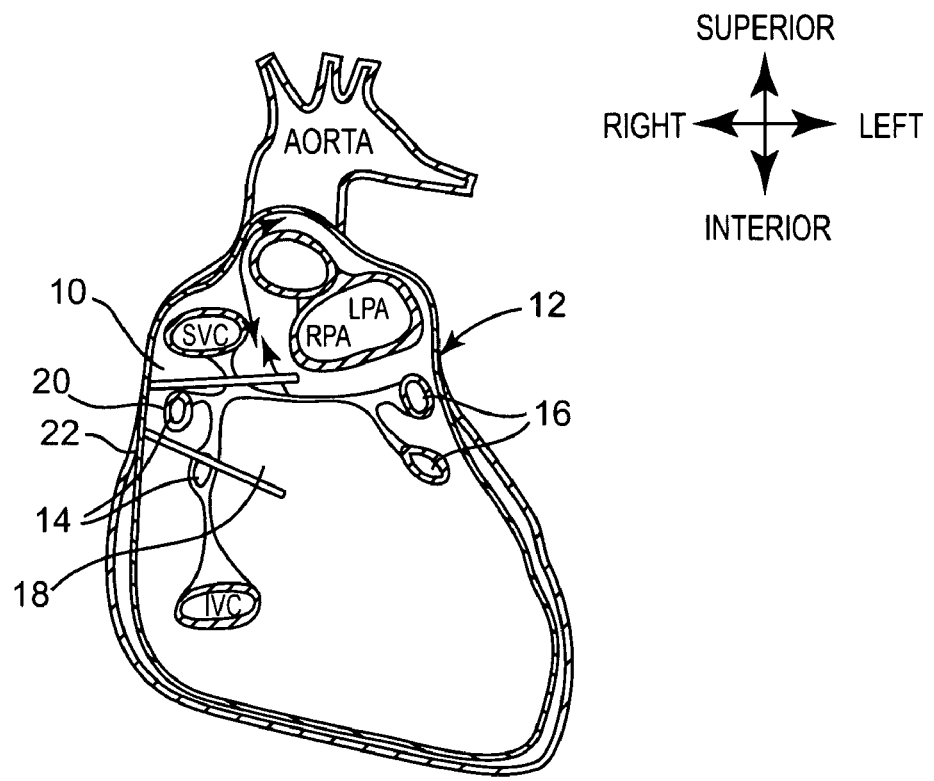
FIG. 1 is a posterior cross-sectional view of a patient's heart and a conventional bipolar ablation device.

FIG. 1 is a posterior cross-sectional view of a patient's heart illustrating atrial tissue 10, pulmonary veins 12, right pulmonary veins 14, left pulmonary veins 16, and the oblique sinus 18. FIG. 1 also illustrates a conventional bipolar ablation device including a superior jaw 20 and an inferior jaw 22. When creating lesions with conventional bipolar clamping-type devices, both jaws 20, 22 (containing electrodes) are manipulated simultaneously through two separate tissue planes, as shown in FIG. 1. For example, if a surgeon wants to ablate around the pulmonary veins 12, one jaw 20 would have to be placed behind the superior vena cava, through the transverse sinus, and over the superior pulmonary veins. Simultaneously, the other jaw 22 would need to be placed behind the inferior vena cava, through the oblique sinus 18 and under the inferior pulmonary veins. This is further complicated by the relatively fixed angle at a hinge joint of the clamping device. As a result, a surgeon has difficulty in simultaneously advancing both jaws 20, 22 into two separate tissue spaces. Although the superior jaw 20 can be manipulated into the transverse sinus, the inferior jaw 22 is hindered from the oblique sinus 18 by the right inferior pulmonary vein 14.

Figure 2:
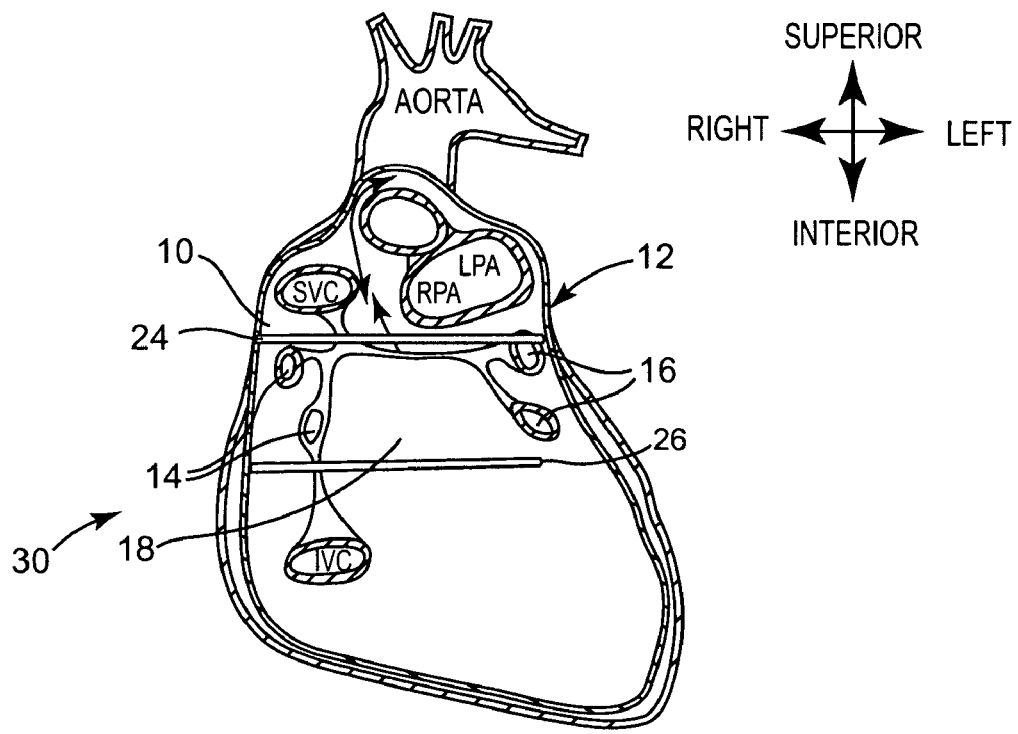
FIG. 2 is a posterior cross-sectional view of a patient's heart and a schematic representation of a compound bipolar ablation device according to one embodiment of the invention.

FIG. 2 is a posterior cross-sectional view of a patient's heart and jaws 24, 26 placed independently into two separate spaces according to one embodiment of the invention. After positioning, both jaws 24, 26 can be joined at a hinge point. This is a less invasive approach, resulting in less trauma to the patient than during a sternotomy. Some embodiments of the invention provide a bipolar ablation device that can produce a narrower lesion than a monopolar. A bipolar ablation device according to some embodiments of the invention can create a long continuous lesion with two separate ablations, without completely occluding blood flow (resulting in less trauma than complete occlusion of the pulmonary veins 12).

Some embodiments of the invention provide an ablation device having separable compound jaws for clamping to apply energy, such as radio frequency energy, to ablate tissue in the heart of a patient suffering from atrial fibrillation. After appropriate dissection, the separable jaws can be placed in the thoracic cavity through an incision. This can be through a thorocotomy, sub-xyphoid incision, sternotomy, or other suitable incisions. Ports may be used to aid insertion, and a positioning device, such as a Starfish positioning device manufactured by Medtronic, Inc., may also be used to lift, rotate, or elevate the heart.

As shown schematically in FIG. 2, using a small incision in the patient's chest, an ablation device 30 can be inserted piecemeal into a position in the patient's chest. The pieces (e.g., jaws 24, 26) can be assembled and manipulated to bring electrodes into contact with a patient's beating heart. Selecting the appropriate configuration of the compound jaws 24, 26 to engage and ablate tissue in the heart, the surgeon can perform the ablation procedure quickly without removal, manipulation, or substitution and reinsertion of the ablation device 30. Some embodiments of the invention provide a clamping ablation device 30 with independent separable jaws 24, 26. Each jaw 24, 26 can be individually manipulated into the appropriate space. Once positioned, the jaws 24, 26 can be brought together to create a bipolar system.

Embodiments of the invention can results in a patient experiencing less trauma because of the minimal invasiveness of delivering the working bipolar ablators to the heart tissue to be treated. Blood contacting devices, such as catheters, may not be used so that the use of biomaterials may not be required.

Embodiments of the invention can allow the surgeon to make narrow, linear ablation lesions quickly to reduce the time the patient is in the procedure. The surgeon can create the lesions deeply in the tissue of the heart while minimizing the damage to surrounding tissue. The creation of a long lesion can be achieved by making contiguous lesions using the ablation device 30. The compound jaws 24, 26 can allow the surgeon to selectively make a lesion using a proximal electrode set, a distal electrode set, or both sets simultaneously, depending on the conditions.

Embodiments of the invention can be adapted to maneuver around tissue that should be protected and minimize removal and reinsertion of different types of ablation devices to quickly achieve the desired ablation of the patient's heart tissue. One embodiment of the invention can be a configurable configuration that can allow the ablation device 30 to be used as a bipolar clamp for creating ablative lesions in three different configurations without removal from the patient's chest.

In general, the bipolar ablation device 30 can minimize the invasive nature of the procedure of ablating tissue in the patient's heart. The method and apparatus of the invention can result in less trauma to the patient and less chance of accidentally damaging the heart and surrounding structures. Embodiments of the invention can minimize trauma to the patient by minimizing the size of the incision required to insert the ablation device 30 through the patient's chest wall. Embodiments of the invention can also minimize the trauma to the patient by making more precise ablations and minimizing unnecessary tissue destruction. Embodiments of the invention can use bipolar ablation which results in narrower lesions and less atrial debulking than traditional monopolar ablation approaches. Embodiments of the invention can also reduce the trauma on the patient by making the procedure achieve its objectives in a shorter time. This is done by allowing the surgeon to create linear lesions in the heart from the epicardial surface of the beating heart.

In some embodiments, a bipolar ablation device 30 in which a grounding electrode is in close proximity to a conductive tip) can create narrower and deeper lesions. The grounding electrode can be approximately the same dimension as the conductive tip, and both electrodes can be used to create the lesion.

Embodiments of the bipolar ablation device 30 can be designed to be used in a minimally-invasive environment (e.g., a mini-thoracotomy or an endoscopic procedure). The ablation device 30 can clamp atrial tissue in a two-step process in order to minimize the time of complete blood flow occlusion while ensuring a continuous lesion. Some embodiments of the invention can use magnets in order to latch two handle halves together in a secure and predetermined orientation. Other embodiments of the invention can use a single cable routed through two separate small jaws, looped around a larger jaw, and then locked to the larger jaw in order to actuate the smaller jaws individually. Once both jaws 24, 26 are appropriately positioned, they can be brought together at a hinge point and along an operating shaft to be assembled. Embodiments of the invention can use magnets, keys, accessory tools, and/or visualization techniques to quickly and securely assemble the pieces in a predetermined relation to each other. After assembly, the jaws 24, 26 may be opened and closed to act as a bipolar ablation device. Removal from the patient after ablation can be done as an assembled unit or after disassembly. In one embodiment, to align the jaws, magnets can be positioned in a hinge area. The operating shaft can be steerable to facilitate insertion and blunt dissection. An appropriate transmurality algorithm may be used to indicate a complete lesion to the surgeon or to terminate power when a lesion is completed. Some embodiments of the ablation device 30 can be inserted from a thorocotomy to simultaneously ablate all the pulmonary veins 12, or the access can be from another incision, such as sub-xyphoid incision. Alternatively, the pulmonary veins 12 may be isolated singularly, in pairs, or in any suitable combination.

The ablation device 30 can be designed to isolate the pulmonary veins 12 for ablating, in some embodiments, the left pulmonary veins 16 separately from the right pulmonary veins 14. The ablation device 30 can include lower jaw assembly 32 and an upper jaw assembly 90. As shown in FIG. 3, the lower jaw assembly 32 can include an elongated arm 34 with a handle 36 on a proximal end 38 of the ablation device 30 and two separate pivoting jaws 42, 62 on the distal end 40 of the ablation device 30.

Figure 6:
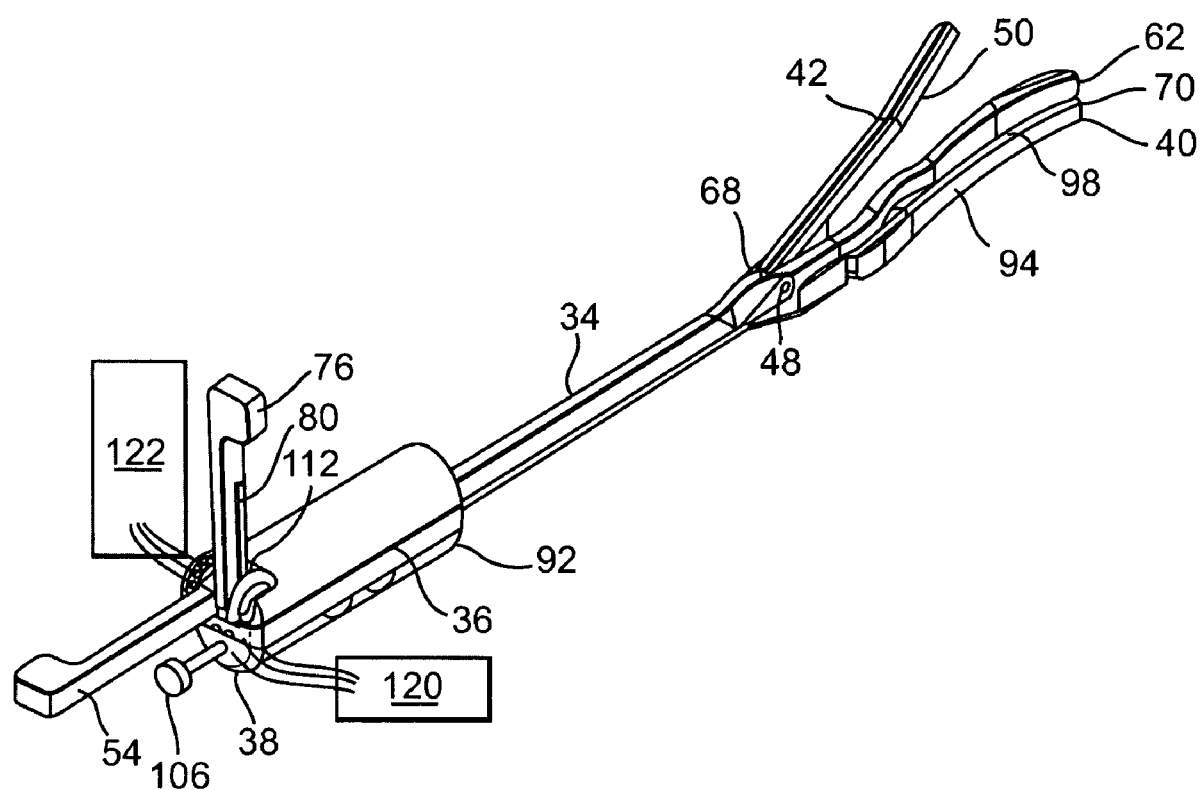
FIG. 6 is a perspective view of the compound bipolar ablation device of FIGS. 4 and 5, including a distal jaw engaged with an upper electrode.

The arm 34 can include a spring-loaded proximal hinge 48 pivotally connecting a proximal jaw 42 to the handle 36. The proximal jaw 42 can include a proximal spring in the proximal hinge 48 for bearing against and maintaining the proximal jaw 42 in an open position. A proximal electrode 50 can be mounted on the proximal jaw 42 for transferring ablation energy to atrial tissue 10. As shown in FIG. 3A, the proximal electrode 50 can include a cover 51 to prevent direct contact with the atrial tissue 10. A supply tube 52 can be in fluid communication with a chamber 58 formed by the cover 51. A proximal supply tube 74 can extend from the handle 36 to a fluid supply 122 (as shown in FIG. 6). A conductor 56 can be mounted on the arm 34 and connected to the proximal electrode 50. The conductor 56 can extend along the lower jaw assembly 32 and can extend from the handle 36 to an ablation energy source 120 (as shown in FIG. 6).

As shown in FIG. 3, adjacent a distal end 40 of the lower jaw assembly 32, a distal jaw 62 can be connected to the arm 34 by a spring-loaded distal hinge 68 to maintain the distal jaw 62 in an open position. The distal jaw 62 can include a distal electrode 70 with a distal cover 72 surrounding the distal electrode 70 to form a chamber 73, as shown in FIG. 3B. A distal supply tube 74 can be positioned on the arm 34 and can be in fluid communication with the chamber 73. The distal supply tube 74 can extend along the lower jaw assembly 32 from the handle 36 to a fluid supply 122 (as shown in FIG. 6). A conductor 78 can be mounted on the arm 34 and can be connected to the distal electrode 70. The conductor 78 can extend along the lower jaw assembly 32 from the handle 36 to an ablation energy source 120 (as shown in FIG. 6).

Figure 4:
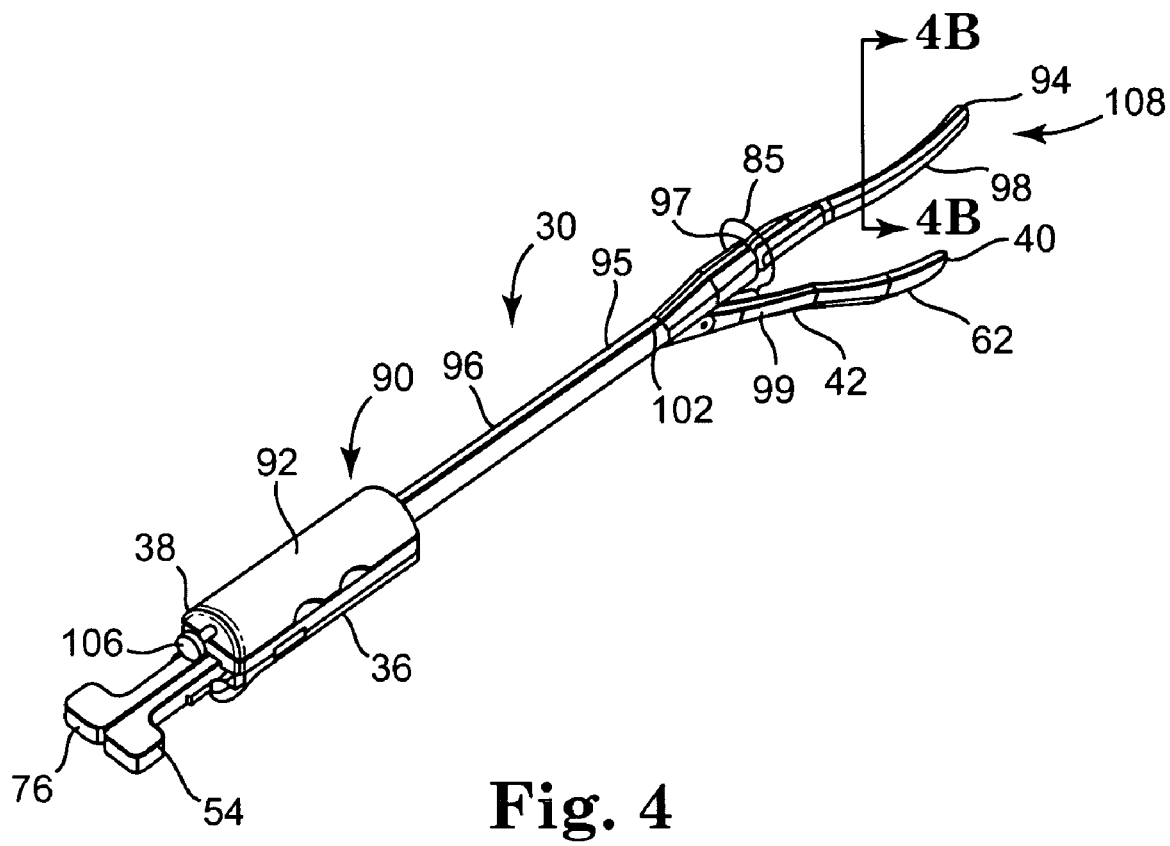
FIGS. 4 and 4A are perspective and cross-sectional views of a compound bipolar ablation device according to one embodiment of the invention, including the lower jaw assembly of FIG. 3 and an upper jaw assembly.

As shown in FIG. 3, the handle 36 can include guides 82 and magnets 83 for assembly and alignment with the upper jaw assembly 90 (as shown in FIG. 4). A proximal jaw actuator 54 can be mounted on the proximal end 36 near the handle 36 and can be connected to the proximal jaw 42 through the proximal jaw hinge 48. The proximal jaw actuator 584 can bear against the spring-loaded proximal jaw hinge 48 to overcome the force holding the proximal jaw 42 in the open position and move the proximal electrode 50 into a tissue engagement position.

A distal jaw actuator 76 can be connected to the distal jaw 62 through the distal jaw hinge 68. The distal jaw actuator 76 can bear against the spring-loaded distal jaw hinge 68 to overcome the spring force and move the distal electrode 70 into a tissue engagement position. As shown in FIG. 3, the distal actuator 76 and the proximal actuator 54 can be connected to a cable loop 85, and can be actuation levers, in one embodiment. Both jaws 42, 62 can be spring-loaded in an open position. The jaws 42, 62 can include electrodes 50, 70. The distal and proximal actuators 54, 76 can be attached to a sliding block (not shown) that can slide parallel to the arm 34. One end of the cable 85 can be attached to the distal actuator 76. The cable 85 can extend along the length of the arm 34 and into the distal jaw 62. The cable 85 can form a loop outside the lower jaw assembly 32 and can then extend into the proximal jaw 42. The cable 85 can then extend back down the arm 34 and can attach to the proximal actuator 54. In other embodiments, the cable 85 can be actuated by a method other than a lever, such as thumb slide, a knob, etc.

After proper dissection, the lower jaw assembly 32 can be placed through an incision or port into the right side of the patient's chest. The lower jaw assembly 32 can be guided into the oblique sinus 18 (as shown in FIG. 2) until the electrodes 50, 70 are positioned around the pulmonary veins 12.

As shown in FIG. 4, the upper jaw assembly 90 can include a handle 92 and an upper arm 96. An upper electrode 98 can be mounted on the upper arm 96 at the distal end 40 of the ablation device 30. The upper arm 96 can be attached to the lower jaw assembly 32 by threading the upper electrode 98 and the adjacent portion of the upper arm 96 through the loop of the cable 85. The handle 92 can include receiving ports for the guides 82 (as shown in FIG. 3) on the handle 36 of the lower jaw assembly 32. A cable slot 97 can be positioned on the upper arm 96 adjacent the upper electrode 98. A conductor 95 can extend from the upper electrode 98 along the upper arm 96 through the handle 92 to the ablation energy source 120 (as shown in FIG. 6). When properly aligned, the handle 36 and the handle 92 can mate with each other, and the loop of the cable 85 can be secured around the upper arm 96 at the cable slot 97 to form an arm clamp 99.

Figure 4A:
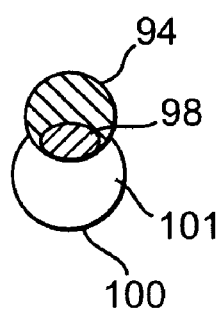

As shown in FIG. 4A, the upper electrode 98 can include a cover 100 that can form a chamber 101. An upper supply tube 102 can be in fluid communication with the chamber 101. The upper supply tube 102 can extend through the upper arm 96 from the handle 92 to the liquid source 122 (as shown in FIG. 6).

The handles 36, 92 of the upper jaw assembly 32 and lower jaw assembly 90 can include one or more magnets 83 that can hold the handles 36, 92 together. The cable 85 can be attached to the arm clamp 99 at the distal end 40 and a clamp actuator 106 at the proximal end 38 of the ablation device 30. The upper electrode 98 can be a single long electrode approximately the same length as the sum of the lengths of the distal electrode 70 and proximal electrode 50. The upper electrode 98 can be aligned with the distal electrode 70 and proximal electrode 50 to form a single bipolar ablating device 108. In some embodiments, the bipolar ablating device 108 can perform ablations in three configurations—upper electrode 98 and distal electrode 70; upper electrode 98 and proximal electrode 50; or upper electrode 98, distal electrode 70, and proximal 50 electrode.

In one embodiment, a distal end of the proximal electrode 50 can be adjacent to a proximal end of the distal electrode 70 on the upper jaw assembly 32. The electrodes 50, 70, 98 can be formed in a particular shape with respect the geometries of the tissue being ablated. The patient's size and age can determine the shape of the electrodes 50, 70, 98.

Figure 5:
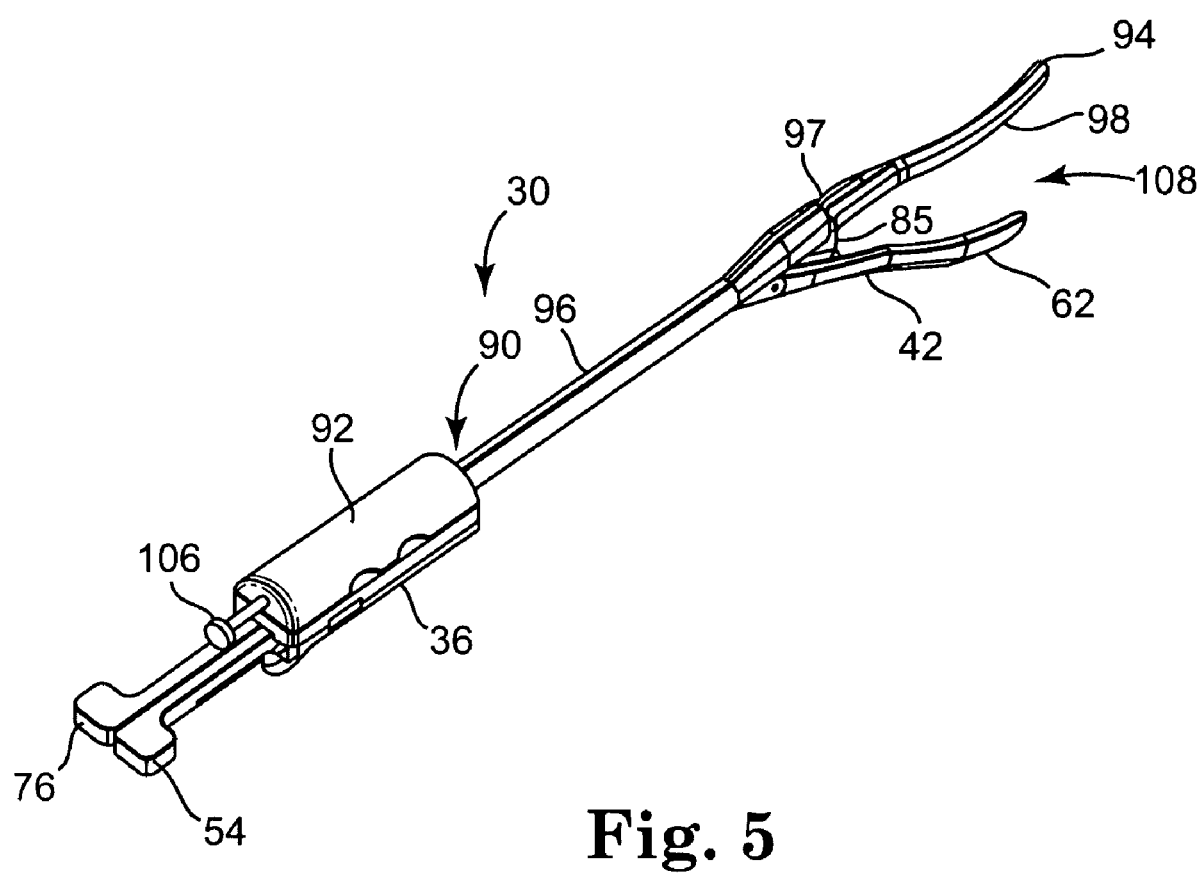
FIG. 5 is a perspective view of the compound bipolar ablation device of FIG. 4 having a cable clamp in a locking position.

As shown in FIG. 5, pulling back on the distal and proximal actuation levers 54, 76 together can tighten the loop of the cable 85 so that it can drop into the cable slot 97. Turning the clamp actuator 106 can lock the cable 85 to the upper jaw 94.

FIG. 6 is a bottom perspective view of the ablating device 30. The operation of the distal actuator 70 is shown pulling the distal electrode 70 toward the upper electrode 98 for clamping the atrial tissue 10 around the left pulmonary veins 16. The proximal jaw 42 can be positioned over the right pulmonary veins 14 allowing some blood flow through the pulmonary veins 12. A ratcheting mechanism 112 can be used to lock the distal actuator 76 in various positions to accommodate different tissue thickness. After ensuring proper placement, the distal electrode 70 can be actuated and the ablation can be performed. The ablating power supply 120 can be connected to the conductors 56, 78, 95 to provide independently controllable energy to each electrode 50, 70, 98, depending on when energization is needed to ablate the atrial tissue 10. The liquid source 122 can be in fluid communication with the chambers 58, 73, 101 of the electrodes 50, 70, 98. A saline liquid can be forced into the chambers 58, 73, 101 to flow through pores in the covers 51, 72, 100. The covers 51, 72, 100 can be constructed of a porous polymer material from a supplier such as Porex Porous Products Group, 500 Bohannon Rd., Fairburn, Ga. 30213-2828. The liquid source 122 can pump a saline or other suitable liquid into the chambers 58, 73, 101 for conducting the ablation energy (such as radio frequency energy) through the covers 51, 72, 100 and into the atrial tissue 10 between the upper electrode 98 and one or both of the proximal electrode 50 and the distal electrode 70.

The proximal actuator 54 can also be rotated to pull the proximal electrode 50 toward the upper electrode 98 in a tissue engagement position that will completely occlude blood flow through the pulmonary veins 12. Use of the proximal electrode 50 can ensure alignment and continuity along the length of the lesion.

As quickly as possible to minimize the time of complete occlusion, a distal release button 80 (as shown in FIG. 6) can be actuated to allow the distal actuator 76 and the electrode 70 to be released and the spring-loaded hinge 68 to move the distal electrode 70 into an open position. The proximal electrode 50 can then be the only electrode in contact with the atrial tissue 10. After ensuring proper placement, the proximal electrode 50 can be activated and the ablation can be performed.

Once the ablation is complete, a proximal release button (not shown) can be actuated to release the proximal electrode 50 from its tissue engagement position and allow the spring-loaded hinge 48 to move the proximal electrode 50 into an open position. The clamp 99 can be released to unlock the cable 85 and allow the upper assembly 90 to be separated from the lower jaw assembly 32.

In operation, the lower jaw assembly 32 can be inserted into the patient through an incision to bring the proximal and distal electrodes 50, 70 into contact with the right and left pulmonary veins 14, 16. The upper jaw assembly 90 can be inserted through the incision or port and guided first through the loop of the cable 85, then through the transverse sinus until the magnets 83 on the handles 36, 92 line up with their corresponding guides 82.

The distal jaw 62 can be used to ablate the atrial tissue adjacent one pulmonary vein first. The tissue adjacent the pulmonary veins can be ablated by the distal electrode 70. To maintain the continuity of the lesion, the proximal jaw 42 can be moved to the closed position to facilitate alignment with the previous lesion and the distal jaw 62 can be released into the open position. The atrial tissue adjacent the other pulmonary veins can be ablated by energizing the proximal electrode 50.

Figure 7:
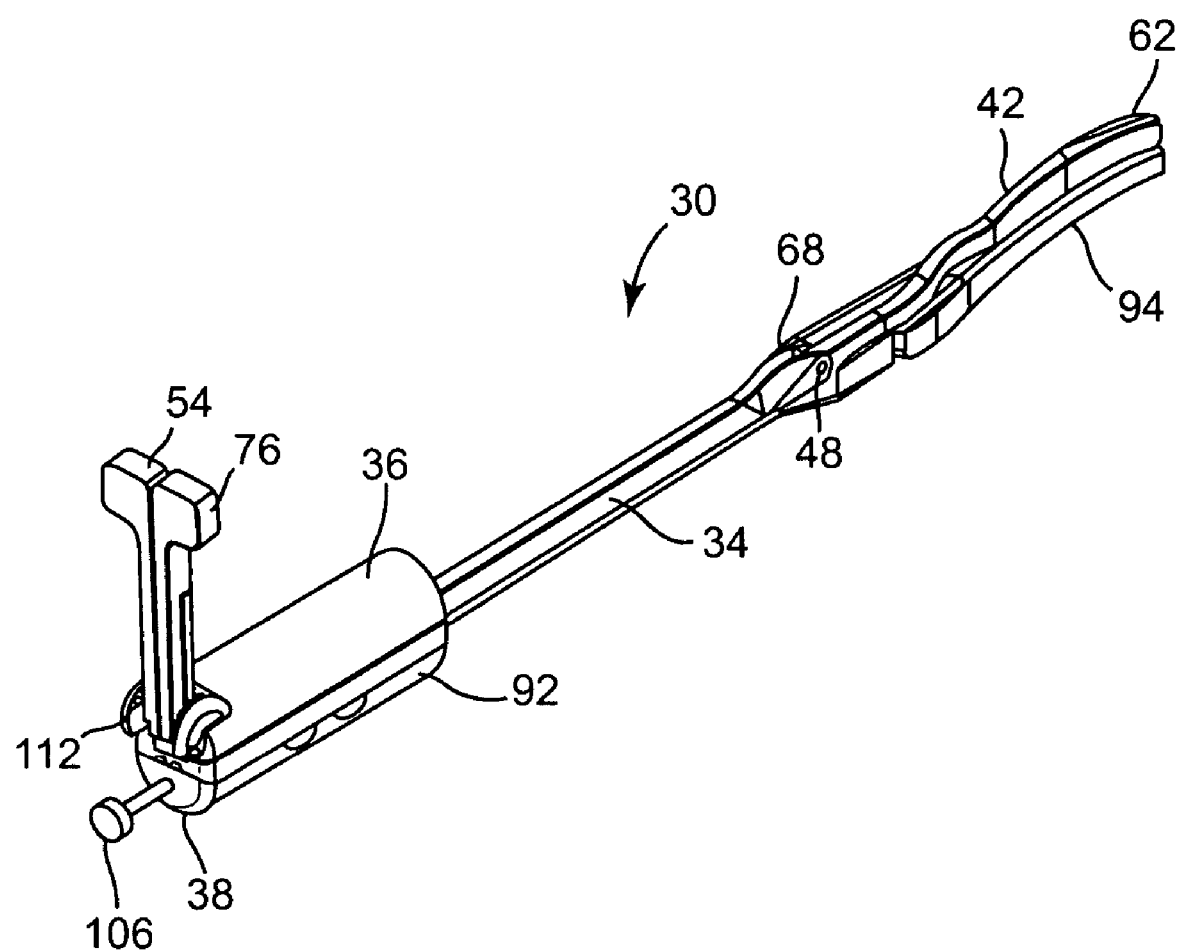
FIG. 7 is a perspective view of the compound bipolar ablation device of FIGS. 4 and 5, including the distal jaw and a proximal jaw engaged with the upper electrode.
Figure 8:
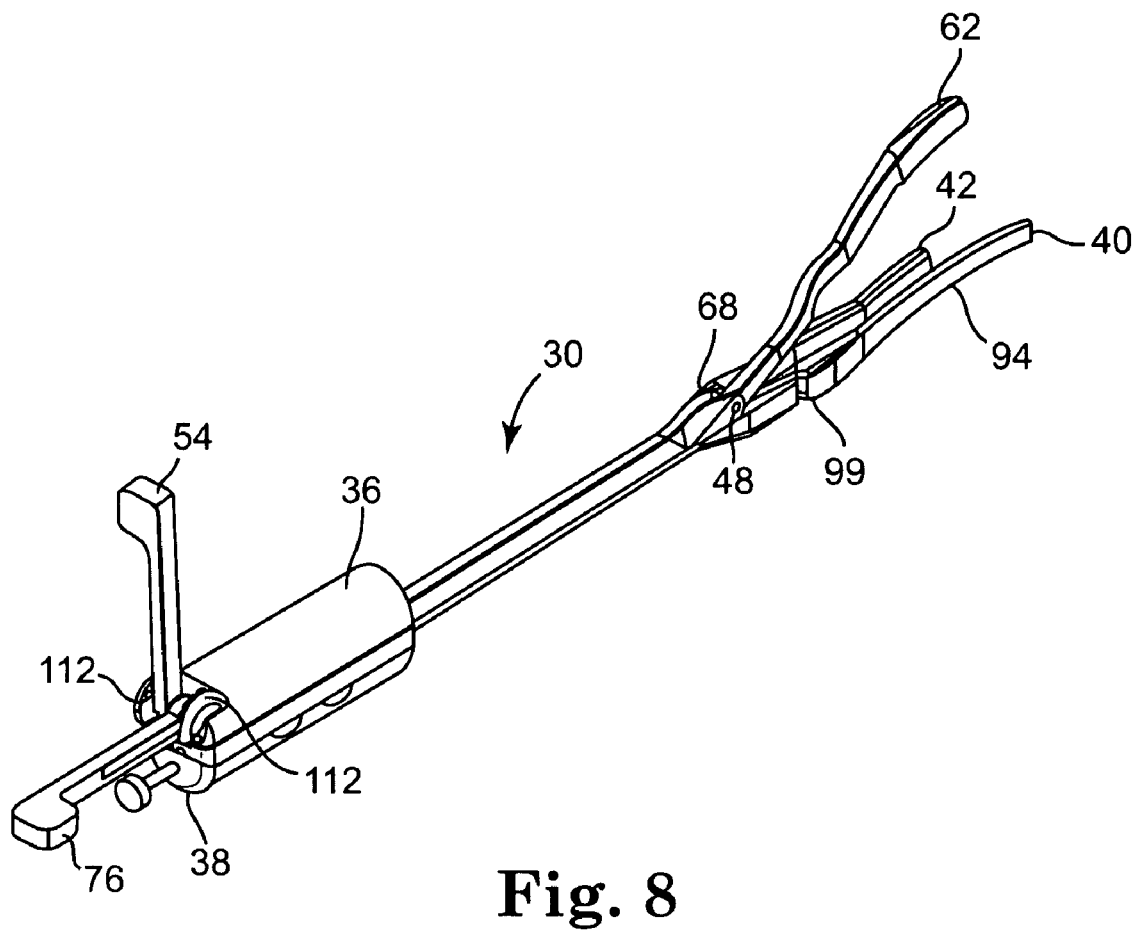
FIG. 8 is a perspective view of the compound bipolar ablation device of FIGS. 4 and 5, including the proximal jaw engaged with the upper electrode.

FIG. 7 illustrates the proximal actuator 54 and the distal actuator 76 positioned to clamp both the proximal jaw 42 and the distal jaw 62 against atrial tissue 10 and/or the upper jaw 94. FIG. 8 illustrates the distal actuator 76 positioned to release the distal jaw 62 and the proximal actuator 54 positioned to clamp the proximal jaw 42.

Figure 9:
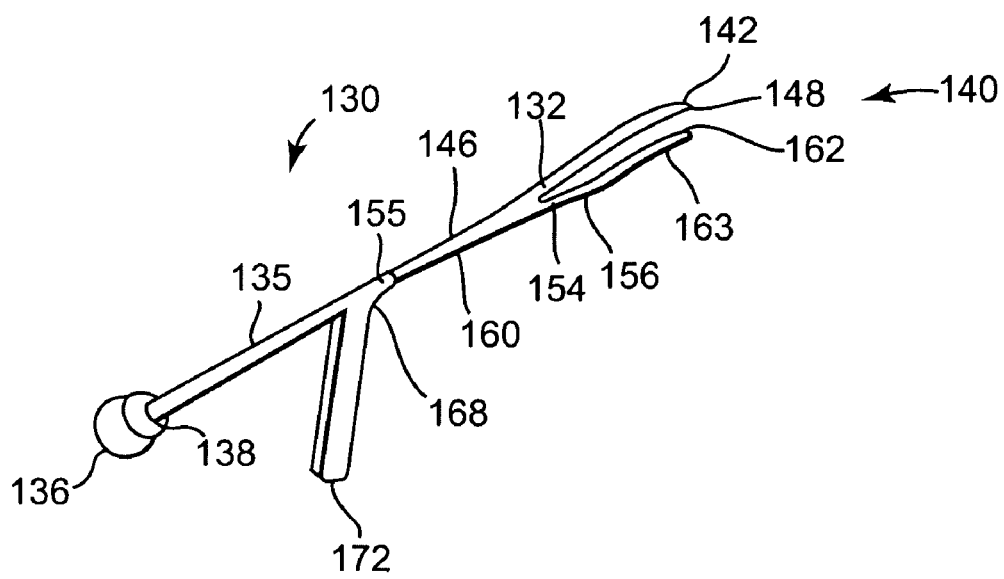
FIG. 9 is a perspective view of a compound bipolar ablation device according to another embodiment of the invention.

As shown in FIG. 9, one embodiment of the ablation device can be a two-piece bipolar ablation device 130 with separable electrodes 148, 162. The two-piece ablation device 130 can use a two-step mechanical process to clamp the atrial tissue 10 around the pulmonary veins 14, 16. The two-piece ablation device 130 can be positioned to clamp around one set of pulmonary valves then the other. The compound ablation device 130 can allow some blood flow and can be used on a beating heart.

The ablation device 130 can include a lower jaw 154 and an upper jaw assembly 132 that can be independent and separable. Each jaw assembly 132, 154 can be individually manipulated into the appropriate space. Once positioned, the jaw assemblies 132, 154 can be brought together to create a bipolar system 140.

The upper jaw assembly 132 can include an upper arm 134 with an upper handle (not shown) on a proximal end 138 and an upper jaw 142 on a distal end 140. A fixed upper jaw hinge 146 or use of a semi-flexible material that can be positioned on the upper arm 134 between the upper handle (not shown) and the upper jaw 142. An upper electrode 148 can be mounted on the upper jaw 142 at the distal end 140. The upper electrode 148 can include a cover (not shown) and a conductor (not shown). The conductor can be connected to the upper electrode 148 and can extend along the upper arm 134 from the upper handle (not shown) to an ablation energy source (not shown). The cover can be positioned over the upper electrode 148 to form a chamber (not shown). An upper supply tube can extend along the upper arm 134 from the handle (not shown) to a liquid source (not shown).

The lower jaw assembly 154 can include an arm 155 having a lower jaw 156 and a lower jaw hinge 160. A lower electrode 162 can be mounted on a distal end 163 of the lower jaw assembly 154. A cover can be positioned over the lower electrode 162 to form a chamber (not shown). A lower supply tube (not shown) can be connected to the chamber and can extend along the lower arm 155 from a lower handle 172 to a liquid source 5. A slider tube 135 can have a handle 136 that can be pushed toward the distal end 140. As the slider tube 135 passes over the upper jaw hinge 146 and lower jaw hinge 160 the upper electrode 148 and lower electrode 162 clamp together.

Figure 10:
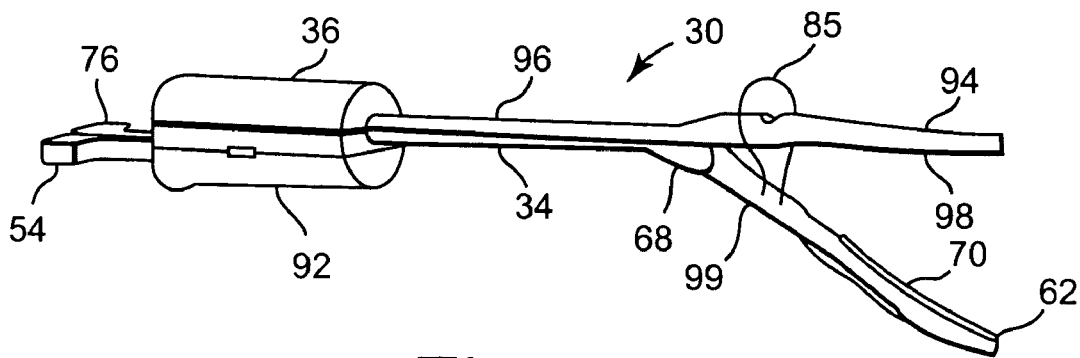
FIGS. 10, 10A, and 10B are perspective views of a compound bipolar ablation device according to another embodiment of the invention.
Figure 10A:
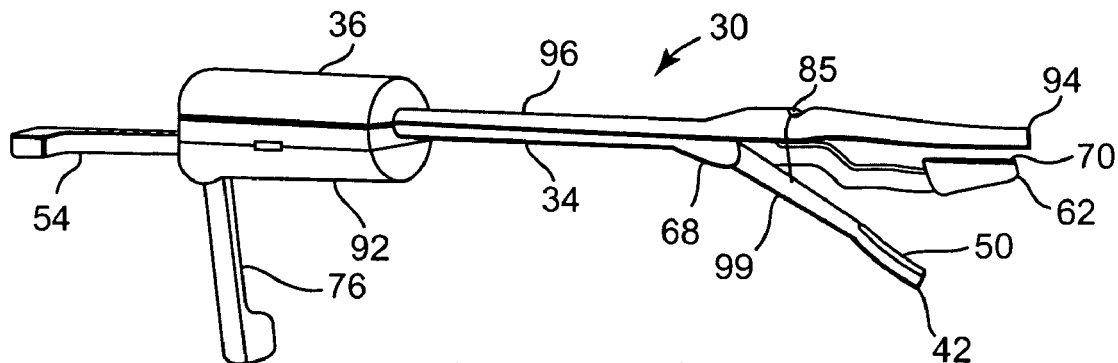
Figure 10B:
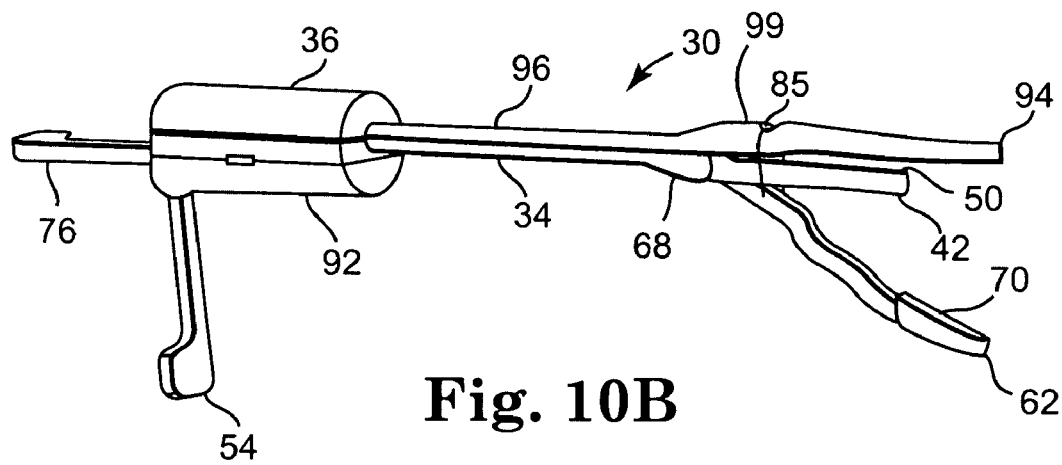

FIGS. 10, 10A, and 10B are additional perspective views of the ablation device 30 in various positions. FIG. 10 illustrates the proximal actuator 54 and the distal actuator 76 in first positions which cause the proximal jaw 42 and the distal jaw 62 to both be open. In FIG. 10, the cable 85 is loose within the arm clamp 99. FIG. 10A illustrates the distal actuator 76 in a second position in which the distal jaw 62 is clamped with respect to the upper jaw 94, the proximal actuator 54 remaining in the first position, and the cable 85 tightened within the arm clamp 99. FIG. 10B illustrates the distal actuator 76 back in the first position, the proximal actuator 54 in the second position in which the proximal jaw 42 is clamped with respect to the upper jaw 94, and the cable 85 tightened within the arm clamp 99.

Figure 11:
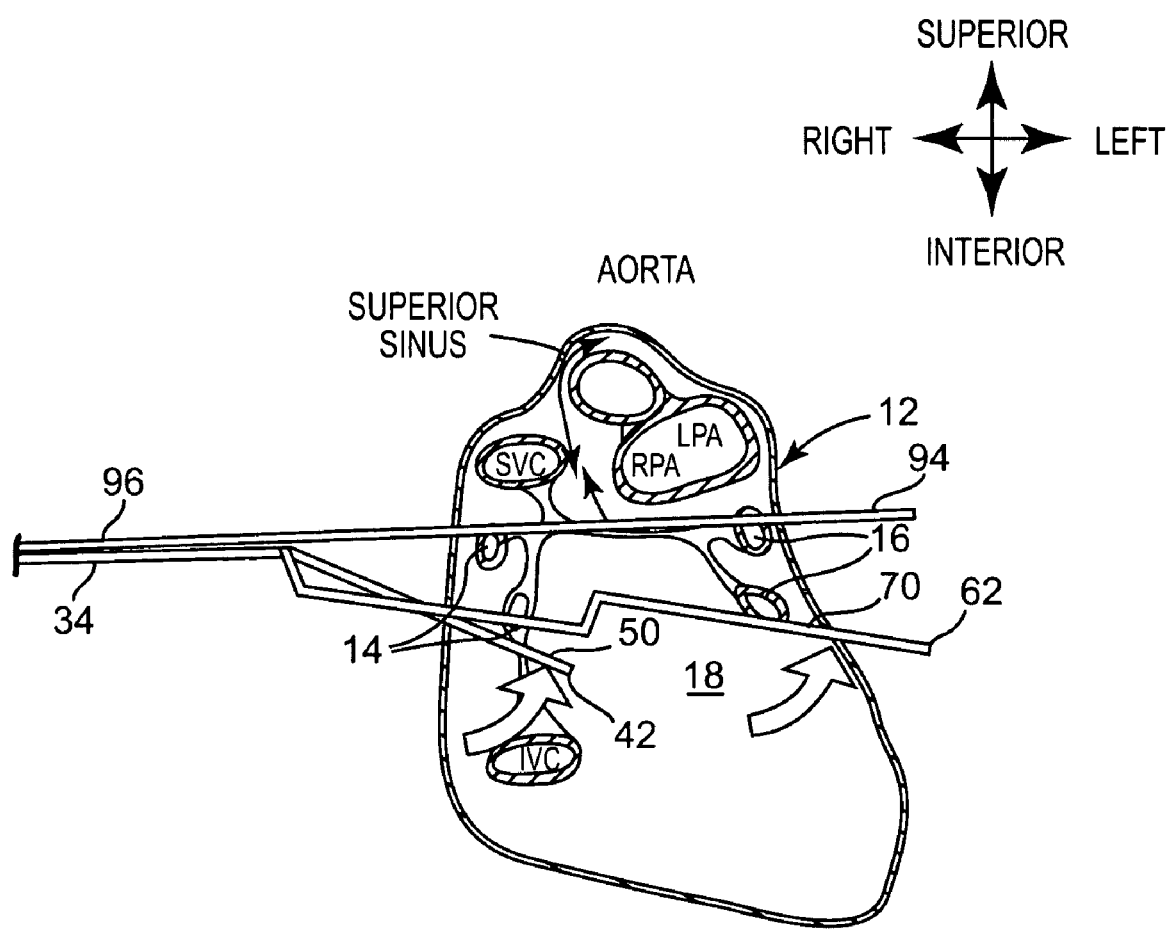
FIG. 11 is a perspective view of a compound bipolar ablation device according to another embodiment of the invention.

FIG. 11 is a schematic illustration of the ablation device 30 within a patient's heart. The upper jaw 94 can be positioned above the superior left and right pulmonary veins 12. The distal jaw 62 can be positioned through the oblique sinus 18 and below the inferior left and right pulmonary veins 12. The proximal jaw 42 can be positioned below the inferior right pulmonary veins 14. The arms 34 and 96 can extend out of an incision in the patient's side.

One embodiment of the invention produces linear radio frequency lesions in the atria using a hemostat device. However, embodiments of the invention can also be used with other energy sources, such as microwave energy, cryogenic energy, thermal energy, etc. Also, embodiments of the invention can be used for creating lesions in other tissues such as lung or liver resections. Additionally, embodiments of the invention can be implemented with various alignment techniques, such as parallel clamping and magnetically-aligned electrodes. The invention can provide a method and embodiments of an ablation device 30 for creating lesions. Such devices are especially useful for ablating on a beating heart, but can also be used on a stopped heart (i.e., during cardiopulmonary bypass).

Various additional features and advantages of the invention are set forth in the following claims.

The invention claimed is:

1. An ablation device for ablating target tissue adjacent pulmonary veins of a patient, the ablation device comprising:
   a first jaw assembly including a proximal jaw having a proximal electrode and a distal jaw having a distal electrode;
   a second jaw assembly movably connected with the first jaw assembly and including an upper jaw having an upper electrode;
   a proximal actuator movable between a first position in which the proximal jaw is open and a second position in which the proximal jaw is positioned in a tissue clamping position with respect to a first portion of the upper jaw; and
   a distal actuator independently movable with respect to the proximal actuator and movable between a first position in which the distal jaw is open and a second position in which the distal jaw is positioned in a tissue clamping position with respect to a second more distal portion of the upper jaw
   wherein at least a portion of the proximal electrode of the proximal jaw when in the tissue clamping position is spaced proximally from the distal electrode of the distal jaw when also in the tissue clamping position for ablating target tissue over a length greater than each of the proximal electrode and the distal electrode alone.

2. The ablation device of claim 1 wherein the proximal electrode, the distal electrode, and the upper electrode are capable of receiving ablation energy individually.

3. The ablation device of claim 1 wherein the at least one of the proximal electrode, the distal electrode, and the upper electrode includes a cover that creates a chamber that receives a liquid.

4. The ablation device of claim 3 wherein the liquid includes saline.

5. The ablation device of claim 1 and further comprising a cable coupled to at least one of the proximal actuator and the distal actuator and coupled to at least one of the proximal jaw, the distal jaw, and the upper jaw.

6. The ablation device of claim 1 wherein the second jaw assembly includes an upper handle and the first jaw assembly includes a lower handle.

7. The ablation device of claim 6 wherein the upper handle is coupled to the lower handle with at least one magnet.

8. The ablation device of claim 1 wherein the second jaw assembly is coupled to the first jaw assembly with a cable that can be moved by a clamp actuator.

9. The ablation device of claim 8 wherein the cable forms a loop that receives the second jaw assembly after the first jaw assembly is positioned within the patient.

10. The ablation device of claim 1 wherein at least one of the proximal actuator and the distal actuator is coupled to a handle with a ratcheting mechanism.

11. The ablation device of claim 1 wherein at least one of the proximal jaw and the distal jaw is coupled to an arm with a biased hinge.

12. The ablation device of claim 1 and further comprising a distal release button coupled to the distal jaw, the distal release button causing the distal jaw to open after a distal ablation.

13. The ablation device of claim 1 wherein the ablation energy includes at least one of radio frequency energy, thermal energy, cryogenic energy, and microwave energy.

14. The ablation device of claim 1 wherein the proximal actuator includes a knob and the distal actuator includes a trigger.

15. The ablation device of claim 1 wherein at least one of the proximal actuator and the distal actuator includes a lever that moves from a first position along an axis of an arm to a second position perpendicular to the axis of the arm.

* * * * *